(12) United States Patent
Mami-Chouaib et al.

(10) Patent No.: US 11,179,449 B2
(45) Date of Patent: Nov. 23, 2021

(54) IMMUNOGENIC PREPROCALCITONIN PEPTIDES

(71) Applicants: Institut Gustave Roussy, Villejuif (FR); Institut National de la Sante et de la Recherche Medicale, Paris (FR); University Paris-Sud, Orsay (FR)

(72) Inventors: Fathia Mami-Chouaib, Bourg la Reine (FR); Aurélie Durgeau, Orsay (FR)

(73) Assignees: Institut Gustave Roussy, Villejuif (FR); Institut National de la Sante et de la Recherche Medicale, Paris (FR); Université Paris-Saclay, Orsay (FR)

( * ) Notice: Subject to any disclaimer, the term of this patent is extended or adjusted under 35 U.S.C. 154(b) by 430 days.

(21) Appl. No.: 15/742,771

(22) PCT Filed: Jul. 4, 2016

(86) PCT No.: PCT/EP2016/065733
§ 371 (c)(1),
(2) Date: Jan. 8, 2018

(87) PCT Pub. No.: WO2017/005702
PCT Pub. Date: Jan. 12, 2017

(65) Prior Publication Data
US 2018/0200355 A1  Jul. 19, 2018

(30) Foreign Application Priority Data
Jul. 9, 2015  (EP) ..................................... 15176174

(51) Int. Cl.
*A61K 39/00* (2006.01)
*A61P 35/00* (2006.01)
*A61K 35/15* (2015.01)
*A61K 45/06* (2006.01)
(52) U.S. Cl.
CPC .......... *A61K 39/0011* (2013.01); *A61K 35/15* (2013.01); *A61K 45/06* (2013.01); *A61P 35/00* (2018.01); *A61K 2039/585* (2013.01)

(58) Field of Classification Search
CPC .... A61K 39/0011; A61K 35/15; A61K 45/06; A61K 2039/585; A61P 35/00
See application file for complete search history.

(56) References Cited

U.S. PATENT DOCUMENTS

2012/0087862 A1* 4/2012 Hood ................. G01N 33/6845
424/9.1

FOREIGN PATENT DOCUMENTS

WO          01/75179 A2    10/2001

OTHER PUBLICATIONS

Sanchez-Trincado et al. Fundamentals and Methods for T- and B-Cell Epitope Prediction. Journal of Immunology Research, 14 pages, published Dec. 28, 2017.*
Luft et al. Exogenous Peptides Presented by Transporter Associated with Antigen Processing (TAP)—Deficient and TAP-Competent Cells: Intracellular Loading and Kinetics of Presentation. Journal of Immunology 167: 2529-2537, 2001.*
Papewalis et al., "Dendritic cell vaccination induces tumor epitope-specific Th1 immune response in medullary thyroid carcinoma," Hormone and Metabolic Research, 40: 108-116 (2008).
International Search Report issued in corresponding International Patent Application No. PCT/EP2016/065733 dated Aug. 5, 2016.
European Search Report issued in corresponding European Patent Application No. 15176174.9 dated Feb. 5, 2016.

* cited by examiner

*Primary Examiner* — Alana Harris Dent
(74) *Attorney, Agent, or Firm* — Morgan, Lewis & Bockius LLP

(57) ABSTRACT

The invention relates to combinations of peptides carrying T-cell epitopes of the antigen preprocalcitonin, presented by the MHC. These peptides can be used in anti-tumour immunotherapy.

13 Claims, 14 Drawing Sheets

Figure 1:
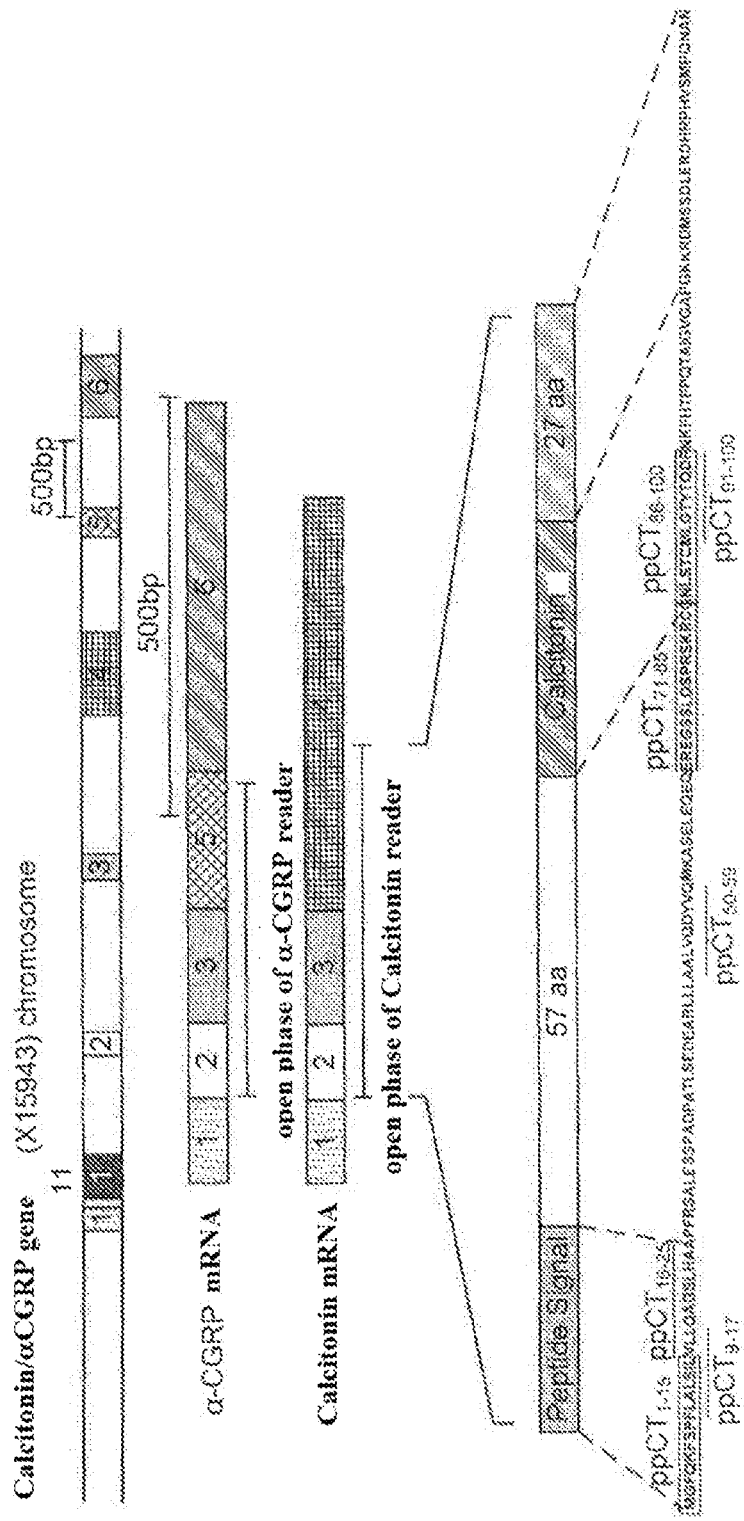

Specification includes a Sequence Listing.

Combination 1: 3 peptides of 15 aa: ppCT$_{1-15}$ ppCT$_{71-85}$ ppCT$_{86-100}$ ppCT$_{1-15}$ — MGFQKFSPFLALSIVLLAQGSLHAAPFRSALESSPADPATLSEDEARLLLAALVQDYVQMKASELEQEQEREGSSLDSPRSKR $\underline{\text{CGNLSTCMLGTYTQD}}$ FNKFHTFPQTAIGVGAP $\underline{\text{KKKDMSSDLERDHRPHVSMPQNAN}}$
$\qquad\qquad$ ppCT$_{71-85}$ $\qquad\qquad$ ppCT$_{86-100}$

Combination 2: 4 peptides, 2 of 15 aa and 2 of 10 aa: ppCT$_{1-15}$ ppCT$_{16-25}$ ppCT$_{50-59}$ ppCT$_{86-100}$ ppCT$_{1-15}$ ppCT$_{16-25}$
$\underline{\text{MGFQKFSPFLALSIV}}$ $\underline{\text{LLAQGSLHAAPFRS}}$ ALESSPADPATLSEDEARLLLAALVQDYVQMKASELEQEQEREGSSLDSPRSKRCGNLSTCMLGTYTQDFNKFHTFPQTAIGVGAP $\underline{\text{KKKDMSSDLERDHRPHVSMPQNAN}}$
$\qquad\qquad\qquad\qquad\qquad\qquad$ ppCT$_{50-59}$ $\qquad\qquad\qquad\qquad\qquad\qquad$ ppCT$_{86-100}$

Combination 3: 4 peptides, 2 of 15 aa and 2 of 10 aa: ppCT$_{1-15}$ ppCT$_{71-85}$ ppCT$_{16-25}$ ppCT$_{50-59}$ ppCT$_{1-15}$ ppCT$_{16-25}$
$\underline{\text{MGFQKFSPFLALSIV}}$ $\underline{\text{LLAQGSLHAAPFRS}}$ ALESSPADPATLSEDEARLLLAALVQDYVQMKASELEQEQEREGSSL $\underline{\text{DSPRSKRCGN}}$ LSTCMLGTYTQDFNKFH $\underline{\text{TFPQTAIGVGAP}}$ KKKDMSSDLERDHRPHVSMPQNAN
$\qquad\qquad\qquad\qquad\qquad\qquad$ ppCT$_{50-59}$ $\qquad\qquad$ ppCT$_{71-85}$

Combination 4: 4 peptides, 1 of 15 aa and 2 of 10 aa: ppCT$_{1-15}$ ppCT$_{71-85}$ ppCT$_{16-25}$ ppCT$_{86-100}$ $\underline{\text{MGFQKFSPFLALSIV}}$ $\underline{\text{LLAQGSLHAAPFRS}}$ ALESSPADPATLSEDEARLLLAALVQDYVQMKASELEQEQEREGSSLDSPRSKR $\underline{\text{CGNLSTCMLGTYTQD}}$ FNKFHTFPQTAIGVGAP $\underline{\text{KKKDMSSDLERDHRPHVSMPQNAN}}$
ppCT$_{16-25}$ $\qquad\qquad\qquad\qquad\qquad\qquad$ ppCT$_{71-85}$ $\qquad\qquad$ ppCT$_{86-100}$

Combination 5: 5 peptides, 3 of 15 aa and 2 of 10 aa: ppCT$_{1-15}$ ppCT$_{71-85}$ ppCT$_{86-100}$ ppCT$_{9-17}$ ppCT$_{16-25}$ ppCT$_{1-15}$ ppCT$_{16-25}$
$\underline{\text{MGFQKFSPFLALSIV}}$ $\underline{\text{LLAQGSLHAAPFRS}}$ ALESSPADPATLSEDEARLLLAALVQDYVQMKASELEQEQEREGSSL $\underline{\text{DSPRSKRCGN}}$ LSTCMLGTYTQDFNKFH $\underline{\text{TFPQTAIGVGAP}}$ KKKDMSSDLERDHRPHVSMPQNAN
ppCT$_{9-17}$

Combination 6: 5 peptides, 2 of 15 aa and 2 of 10 aa and 1 of 9 aa: ppCT$_{1-15}$ ppCT$_{71-85}$ ppCT$_{86-100}$ ppCT$_{9-17}$ ppCT$_{16-25}$ ppCT$_{1-15}$ ppCT$_{16-25}$
$\underline{\text{MGFQKFSPFLALSIV}}$ $\underline{\text{LLAQGSLHAAPFRS}}$ ALESSPADPATLSEDEARLLLAALVQDYVQMKASELEQEQEREGSSLDSPRSKR $\underline{\text{CGHLSTCMLGTYTQD}}$ FNKFHTFPQTAIGVGAP $\underline{\text{KKKDMSSDLERDHRPHVSMPQNAN}}$
ppCT$_{9-17}$ $\qquad\qquad\qquad\qquad\qquad\qquad$ ppCT$_{86-100}$

*Fig. 3*

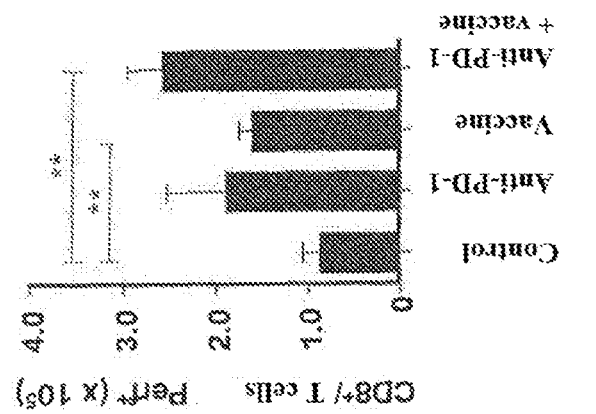
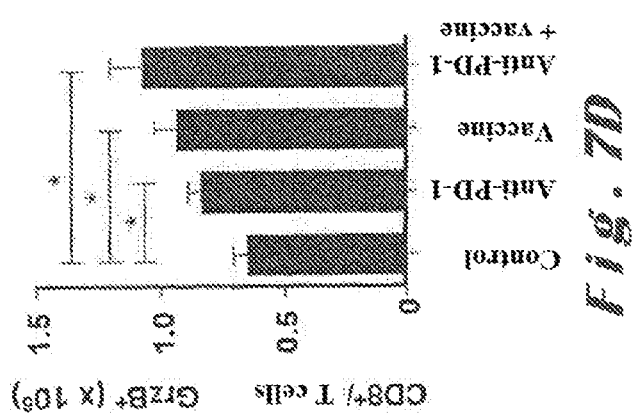
Fig. 7D
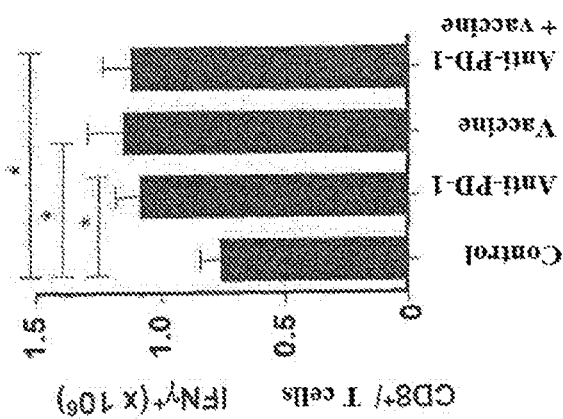

IMMUNOGENIC PREPROCALCITONIN PEPTIDES

SEQUENCE LISTING SUBMISSION VIA EFS-WEB

A computer readable text file, entitled "SequenceListing.txt," created on or about Jan. 5, 2018 with a file size of about 5 kb contains the sequence listing for this application and is hereby incorporated by reference in its entirety.

The present invention relates to combinations of epitopes of preprocalcitonin (ppCT) and their use in antitumour immunotherapy.

Vaccination or peptide immunotherapy is a therapeutic approach that is currently the subject of great interest in the field of prevention or treatment of cancers. The principle is based on immunisation by peptides reproducing T-cell epitopes of tumour antigens recognised by the cytotoxic T lymphocytes (CTL), which play a major role in the elimination of cancerous cells expressing these antigens at their surface.

It will be recalled that the CTL do not recognise whole protein antigens, but rather the peptide fragments of same, presented by molecules of the major histocompatibility complex (MHC) expressed at the surface of various cells. These are the peptide fragments which constitute the T-cell epitopes.

The presentation of these peptides results from a complex process, called "antigen processing", which involves three main steps:
- cytosolic degradation of antigens by a multienzyme complex called proteasome;
- the translocation of peptides resulting from this degradation in the endoplasmic reticulum (ER) by TAP transporters;
- association of these peptides with the MHC in order to form stable peptide/MHC complexes, which are exported to the cell surface.

The epitopes presented by the class I major histocompatibility complex (MHC I) have generally 8 to 11 amino acids (aa) and are recognised by the CD8+ T cells, which represent the major component of the cytotoxic response. The epitopes presented by the class II major histocompatibility complex (MHC II) have generally 13 to 18 amino acids and are recognised by the CD4+ T cells.

Identification of these epitopes is an essential step for the development of antitumour immunotherapy compositions.

Preprocalcitonin is coded for by the CALCA gene, which also codes for the alpha form of a neuropeptide, the "calcitonin gene-related peptide" (α-CGRP). This gene contains 5 introns and 6 exons, and its primary transcript is the subject of an alternative tissue-specific splicing. The exon junctions 1, 2, 3 and 4 produce calcitonin mRNA in the C cells of the thyroid, while those of exons 1, 2, 3, 5 and 6 produce α-CGRP mRNA in the neurons (MORRIS et al., Nature, 308, 746-8, 1984).

Calcitonin mRNA codes for a precursor with 141 amino acids, preprocalcitonin, which contains an N-terminal signal sequence of 25 residues, the cleaving of which produces 116-aa procalcitonin. Procalcitonin comprises an N-terminal region of 57 aa, followed by mature 32-aa calcitonin, a 21-aa C-terminal peptide, katacalcin (ROSENFELD et al., Nature, 304, 129-35, 1983). The mature form of α-CGRP is a 37-aa peptide, with vasodilator effect, found in a large number of tissues (ZAIDI et al., Crit Rev Clin Lab Sci, 28, 109-74, 1990). The preprocalcitonin signal sequence is also found in the preprohormone α-CGRP.

The physiological role of calcitonin is mainly to protect the skeleton during periods of "calcium stress", such as growth, pregnancy and lactation. Calcitonin it also produced in large quantities by medullary thyroid carcinoma (MTC) cells and certain pulmonary carcinomas (COOMBES et al., Lancet, 1, 1080-3, 1974; MILHAUD et al., Lancet, 1, 462-3, 1974). High levels of plasma calcitonin are diagnostic and prognostic markers in these tumours.

The use of dendritic cells pulsed with mature calcitonin has been proposed for MTC immunotherapy (SCHOTT et al., Cancer Immunol Immunother, 51, 663-8, 2002). More recently, the inventors' team has identified a 10-amino-acid antigenic peptide derived from preprocalcitonin signal peptide. This peptide corresponds to an epitope processed in the endoplasmic reticulum by a mechanism that is independent of proteasome and TAP transporters (patent application WO2009010874).

The inventors have now identified other regions of preprocalcitonin involved in inducing an antitumour immune response, and have shown that the combination of different epitopes enables a better antitumour response.

The present invention relates to a composition comprising at least two peptide sequences chosen from:
- MGFQKFSPFLALSIL (SEQ ID NO: 1), also referred to hereinafter as ppCT1-15;
- EREGSSLDSPRSKRC (SEQ ID NO: 2), also referred to hereinafter as ppCT71-85;
- GNLSTCMLGTYTQDF (SEQ ID NO: 3), also referred to hereinafter as ppCT86-100;
- FLALSILVL (SEQ ID NO: 4), also referred to hereinafter as ppCT9-17;
- VLLQAGSLHA (SEQ ID NO: 5), also referred to hereinafter as ppCT16-25;
- LLAALVQDYV (SEQ ID NO: 6), also referred to hereinafter as ppCT50-59;
- CMLGTYTQDF (SEQ ID NO: 7), also referred to hereinafter as ppCT91-100;
- EARLLLAALVQDYVQ (SEQ ID NO: 8), also referred to hereinafter as ppCT45-60;
- MGFQKFSPFL (SEQ ID NO: 9), also referred to hereinafter as ppCT1-10;
- FQKFPFLAL (SEQ ID NO: 10), also referred to hereinafter as ppCT3-12;
- KFSPFLALSI (SEQ ID NO: 11), also referred to hereinafter as ppCT5-14;
- FSPFLALSIL (SEQ ID NO: 12), also referred to hereinafter as ppCT6-15;
- NLSTCMLGTY (SEQ ID NO: 13), also referred to hereinafter as ppCT87-96;
- LSTCMLGTYT (SEQ ID NO: 14), also referred to hereinafter as ppCT88-97;
- YTQDFNKFHT (SEQ ID NO: 15), also referred to hereinafter as ppCT96-105;
- TLSEDEARLL (SEQ ID NO: 16), also referred to hereinafter as ppCT41-50;
- ALVQDYVQMK (SEQ ID NO: 17), also referred to hereinafter as ppCT53-62; and
- YVQMKASEL (SEQ ID NO: 18), also referred to hereinafter as ppCT58-66.

In a composition according to the invention, each of said sequences is present either in the form of a peptide of 8 to 15 amino acids, or is included in an multiepitope chimeric polypeptide. A chimeric polypeptide is defined here as a series of amino acids which is not present in nature. A chimeric polypeptide as understood here, can comprise at least two sequences chosen from sequences of SEQ ID NOs: 1 to 18, said sequences being, in said polypeptide, adjacent, linked by a linking element consisting of 1 to 5 amino acids, or separated by a sequence comprising an epitope of a protein other than preprocalcitonin.

The compositions according to the invention are therefore multiepitopes, and are preferably capable of generating a polyspecific response, in at least some individuals.

According to a preferred embodiment of the invention, the composition comprises at least one sequence corresponding to an epitope processed in the endoplasmic reticulum by a mechanism that is independent of proteasome and TAP transporters, such as sequences of SEQ ID NOs: 4 and 5. Yet more preferably, the composition further comprises at least one sequence corresponding to an epitope processed in the endoplasmic reticulum by a mechanism that is dependent on proteasome and TAP transporters, such as sequences of SEQ ID NOs: 3 and 6. The composition according to the invention preferably comprises the sequence of SEQ ID NO: 6, either in the form of a peptide consisting of this sequence, or included in a chimeric polypeptide as defined above.

According to a particular embodiment of the invention, the composition comprises a mixture of peptides of 9 to 15 amino acids. This mixture can be freeze-dried or in suspension in a solution suitable for pharmaceutical use.

According to another preferred embodiment of the invention, the composition comprises a chimeric polypeptide comprising at least two sequences chosen from the sequences of SEQ ID NOs: 1 to 18, said sequences being adjacent, linked by a linking element consisting of 1 to 5 amino acids, or separated by a sequence comprising an epitope of a protein other than preprocalcitonin. If applicable, the chimeric polypeptide can comprise a plurality of copies of the same sequence. Also, in a chimeric polypeptide according to the invention, at least a part of the immunogenic sequences can be inserted in the adenylate cyclase (AC) of *Bordetella pertussis*. Since the AC receptor is the same as that for CD11b, and since the dendritic cells express the CD11b receptor, such a structure makes it possible to directly direct an immunogenic epitope towards the dendritic cells. (DADAGLIO et al., Int. Immunol, 15, 1423-1430, 2003).

The composition according to the invention optionally comprises at least one other peptide sequence, different from the preceding sequences, in particular a sequence capable of binding to an HLA molecule, for example HLA-B7, such as one of the sequences of SPFLALSIL (SEQ ID NO: 19 or ppCT7-15), EARLLLAAL (SEQ ID NO: 20 or ppCT46-54), and/or SPRSKRCGNL (SEQ ID NO: 21 or ppCT79-88), said peptide sequence being in the form of an isolated peptide or included in a multiepitope chimeric peptide according to the invention.

In order to be widely usable on a population comprised of individuals carrying different HLA alleles, a multiepitope composition according to the invention can comprise epitopes presented by different MHC molecules.

According to a preferred embodiment of the invention, the composition also comprises at least one immune checkpoint inhibitor, such as, in a non-restrictive manner, an anti-PD-1, an anti-PDL-1 or an anti-CTLA4, in particular an antibody, preferably monoclonal, directed against the molecule PD-1, PDL-1 or CTLA4, preferably the human molecule hPD-1, hPDL-1 or hCTLA4. The composition according to the invention advantageously comprises an anti-PD-1, in particular an anti-PD-1 monoclonal antibody, preferably anti-hPD-1.

A chimeric polypeptide according to the invention can be easily obtained by methods known per se, and in particular by conventional recombinant DNA techniques.

A composition according to the invention preferably comprises at least two peptide sequences chosen from the sequences of SEQ ID NOs: 1 to 7, and more preferably at least 3 of these sequences. The position of the peptides of SEQ ID NO: 1-7 with respect to the complete sequence of preprocalcitonin is illustrated in FIG. 1.

Non-limiting examples of sequence combinations present in a composition according to the invention include the following combinations:

the combination of sequences of SEQ ID NOs: 1, 2, 3, 5 and 6;

the combination of sequences of SEQ ID NOs: 1, 3, 4, 5 and 6;

the combination of sequences of SEQ ID NOs: 1, 2, 5 and 6;

the combination of sequences of SEQ ID NOs: 1, 3, 5 and 6;

the combination of sequences of SEQ ID NOs: 3, 4, 5 and 6; the combinations comprising the preceding sequences and at least one immune checkpoint inhibitor such as defined above, in particular an anti-PD-1 monoclonal antibody, preferably an anti-hPD-1 antibody, and/or one of the sequences of SEQ ID NO: 19, 20 and/or 21.

The present invention also relates to nucleic acid molecules coding for a mixture of immunogenic peptides or for a chimeric polypeptide such as defined above, as well as compositions comprising same. These polynucleotides can be inserted in an expression vector, under transcriptional control or an appropriate promoter, in order to enable the expression of the immunogenic peptide or of the chimeric polypeptide according to the invention in a cell or host organism. The choice of the expression vector depends in particular on the cell or organism (prokaryote or eukaryote) where the expression is desired. If it is planned to administer the polynucleotide directly to a patient to be treated, then a naked DNA plasmid is preferably used, or a vector allowing a transient expression, for example a vector derived from an adenovirus or a vaccinia virus. The present invention therefore also relates to a composition comprising at least one nucleic acid molecule coding for at least two peptides of 9 to 15 amino acids chosen from the sequences of SEQ ID NOs: 1 to 18 or coding for a chimeric polypeptide as described above.

Other compositions according to the invention can also comprise dendritic cells, loaded with a peptide or a multiepitope composition of the invention, or transformed with a polynucleotide of the invention, inserted in an appropriate expression vector. They can also comprise artificial antigen-presenting cells loaded with a peptide or a multiepitope composition of the invention. The artificial antigen-presenting cells can be, in particular, vesicles derived from tumour cells (texosomes) described in application PCT WO 1999/003499, or exosomes derived from dendritic cells, as described in the publication of VIAUD et al. (J Immunother, 34, 65-75, 2011).

Another aspect of the present invention is the use of the compositions described above as a drug, in particular as a drug intended for antitumour immunotherapy, more particularly in the treatment of tumours expressing calcitonin and/or α-CGRP. This includes, in particular, small-cell or non-small cell pulmonary carcinomas, as well as medullary thyroid carcinomas. The compositions according to the invention can also be used for the treatment of pathologies associated with a high serum level of calcitonin or procalcitonin or pro α-CGRP, such as the following cancerous pathologies: renal cancer, breast cancer, gastrointestinal cancer (TABOLLI et al, Tumori, 69, 227-230, 1983), pancreatic cancer, prostate cancer (SIM et al, Ann Clin Lab Sci., 26, 487-95, 1996), liver cancer (CONTE et al, Acta Endocrinol, 106, 109-11, 1984) or chronic myeloid leukaemia (TAKUBO et al Haematologia, 31, 177-9, 2001), acute undifferentiated and myeloblastic leukaemia (KIEFER et al, Leuk Lymphoma., 13, 501-507, 1994), neuroendocrine tumours and liver cancer (GHILLIANI et al, Cancer Res, 49, 6845-6851, 1989).

A composition according to the invention can be used in a particularly advantageous manner for immunotherapy of a tumour, the cells of which do not express TAP peptide transporters.

The compositions described above are particularly suitable for the treatment of an HLA-A*0201 patient.

The present invention also relates to the use of a multi-epitope composition of at least two immunogenic peptide epitopes, or a nucleic acid molecule according to the invention in order to obtain a drug, and in particular a drug intended for antitumour immunotherapy, and in particular for the treatment of tumours expressing calcitonin and/or α-CGRP. This includes, in particular, small-cell or non-small cell pulmonary carcinomas, as well as medullary thyroid carcinomas. Said drug can also be used for the treatment of pathologies associated with a high serum level of calcitonin or precalcitonin or prepro α-CGRP, such as the following cancerous pathologies: renal cancer, breast cancer, gastrointestinal cancer (TABOLLI et al, Tumori, 69, 227-230, 1983), pancreatic cancer, prostate cancer (SIM et al, Ann Clin Lab Sci., 26, 487-95, 1996), liver cancer (CONTE et al, Acta Endocrinol, 106, 109-11, 1984) or chronic myeloid leukaemia (TAKUBO et al Haematologia, 31, 177-9, 2001), acute undifferentiated and myeloblastic leukaemia (KIEFER et al, Leuk Lymphoma., 13, 501-507, 1994), neuroendocrine tumours and liver cancer (GHILLIANI et al, Cancer Res, 49, 6845-6851, 1989).

The present invention also includes drugs comprising, as the active substance, at least one immunogenic peptide, a composition, or a nucleic acid molecule according to the invention.

According to a preferred embodiment of the present invention, said drugs are vaccines, in particular therapeutic vaccines.

The drugs according to the invention can further comprise common excipients, as well as adjuvants that are routinely used in an immunotherapy, and promoting, for example, the administration of the active substance, stabilising same, increasing the immunogenicity of same, etc. Examples of usable adjuvants include the CpG oligodeoxynucleotides, apoptosis-inducing factor (AIF), heat shock proteins (HSP), toll-like receptors (TLRs) such as TLR3 agonists (Poly I:C), cytokines and chemokines such as IL-7, IL-12, IL-15 and GM-CSF and CCL5 (RANTES).

The present invention will be better understood with the help of the following additional description, which refers to non-limiting examples illustrating the identification of mixtures of immunogenic peptides according to the invention.

LIST OF FIGURES

FIG. 1: position of the peptides of SEQ ID NOs: 1-7 with respect to the complete sequence of preprocalcitonin.

Figure 2A:
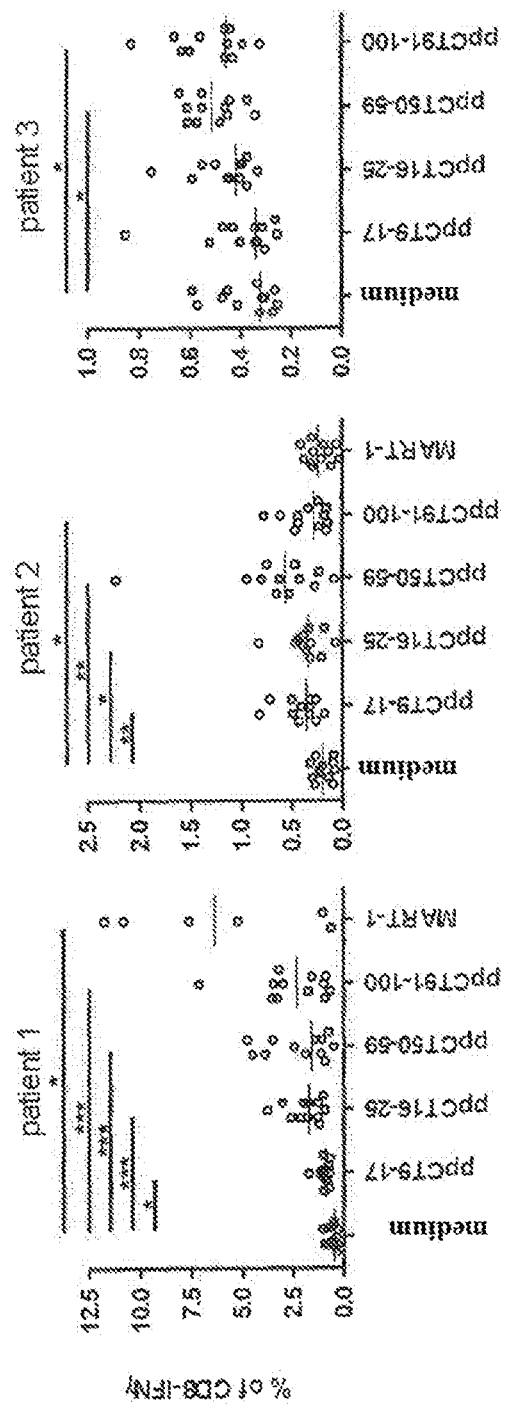
Figure 2B:
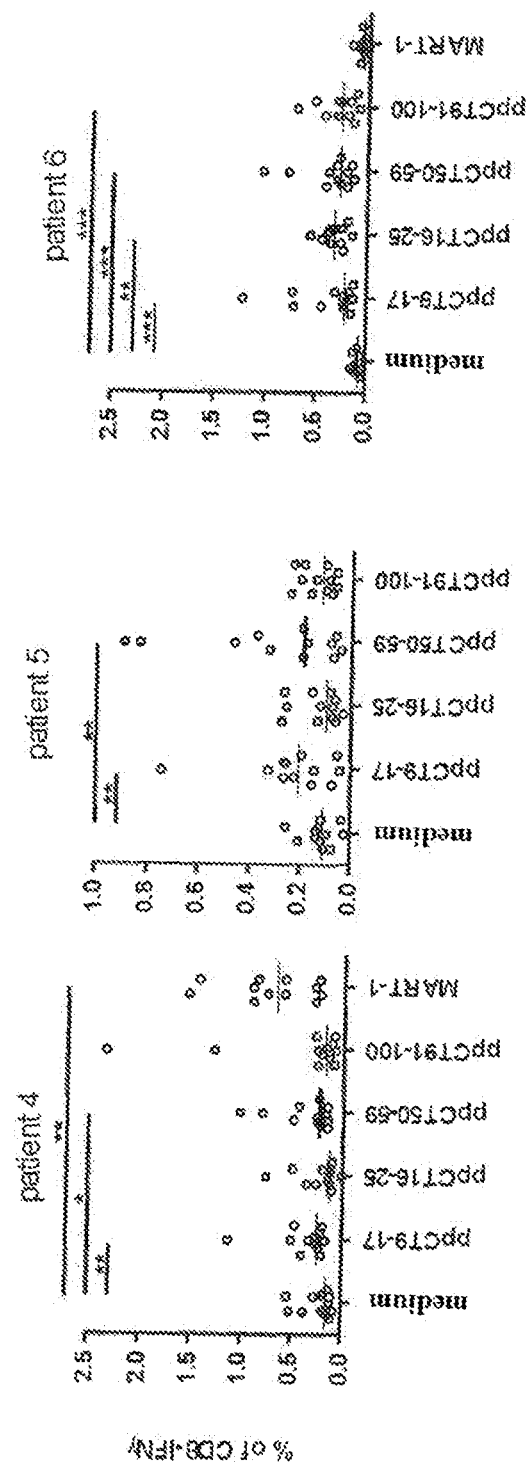
Figure 2C:
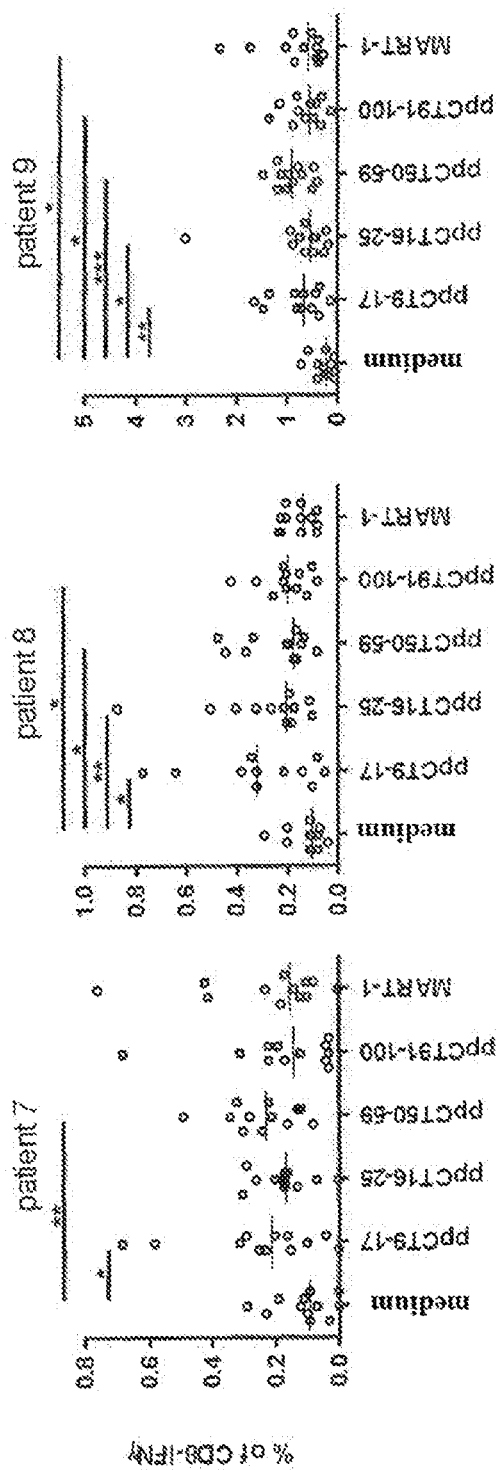

FIG. 2: in vitro stimulation of PBMC of patients using peptides of SEQ ID NOs: 4-7. A to C: the PBMC of 9 patients with non-small cell lung cancer (NSCLC) were each stimulated with 4 peptides and then the number of $CD8^+$/$IFN\gamma^+$ cells was analysed by flow cytometry. Each point (n) corresponds to 8 independent stimulation wells. The median of these points is represented for each patient and each peptide (n=12). The statistically significant increases are indicated (*$p<0.05$; $p<0.01$; *$p<0.005$).

FIG. 3: summary of the different peptide combinations tested in vitro and in vivo in a transgenic mouse model for HLA-A2 molecules.

Figure 4A:
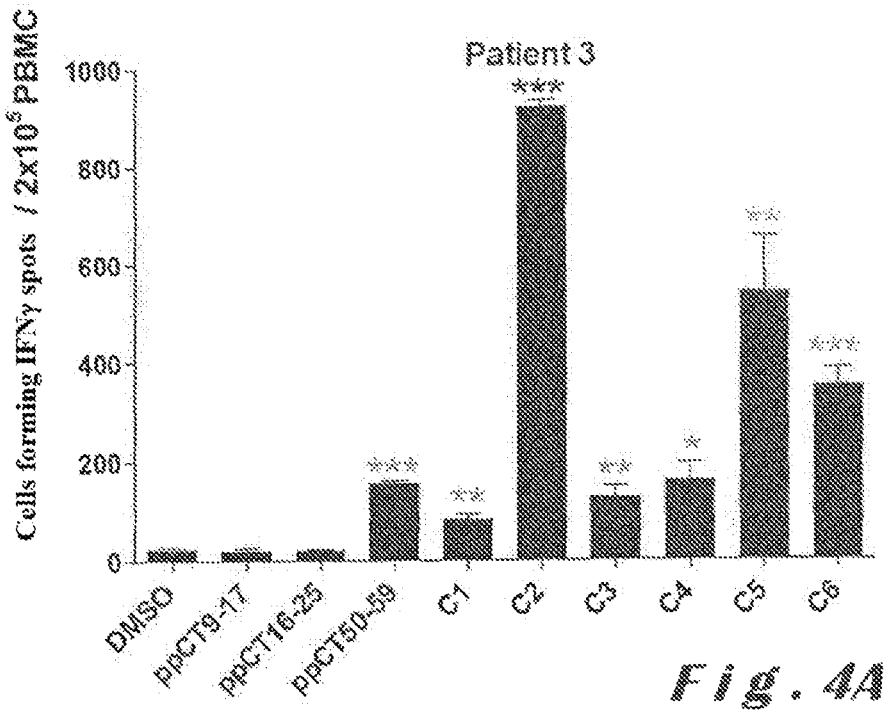
Figure 4B:
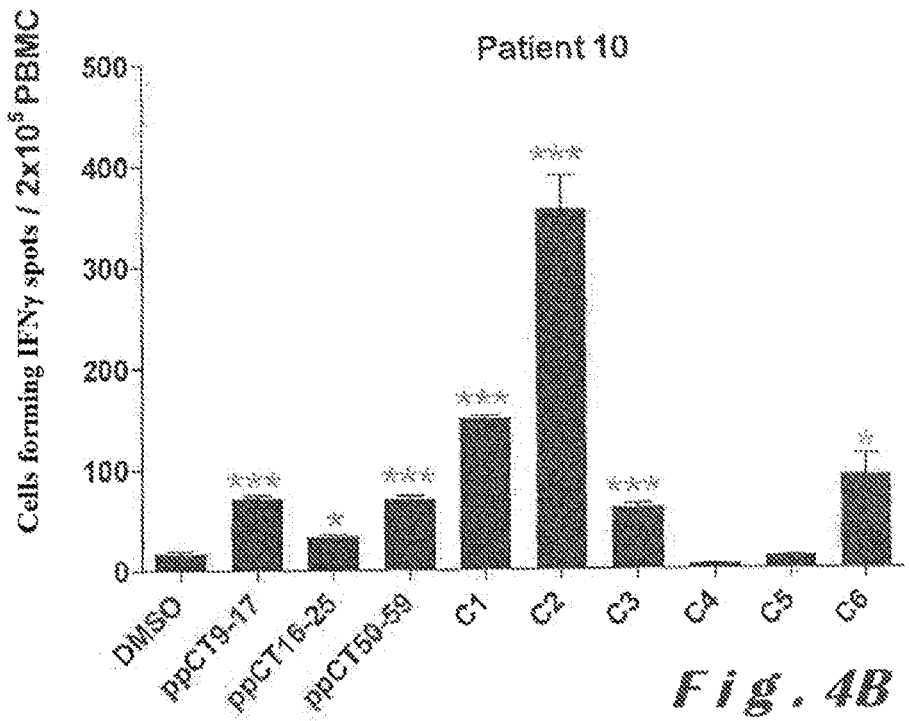
Figure 4C:
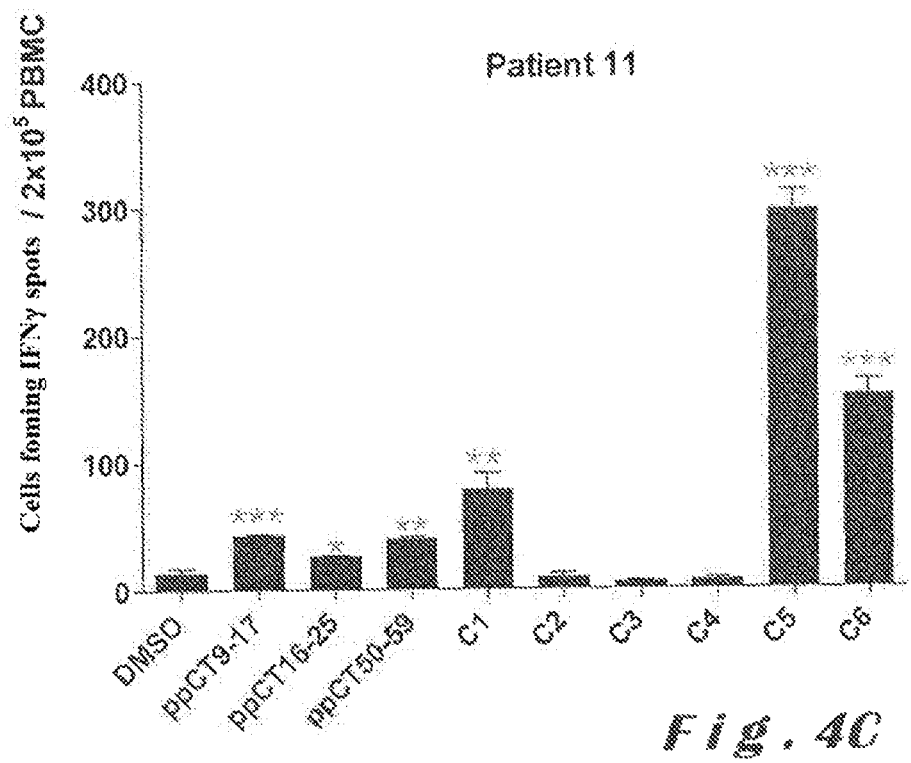

FIG. 4: in vitro stimulation of PBMC of patients with short peptides of 9-10 amino acids or the different peptide combinations. A to C: the PBMC of patients 3 (A), 10 (B) and 11 (C) was stimulated either with one of the peptides of SEQ ID NO: 4 to 6, alone, or with one of the combinations 1 to 6 described in FIG. 3; the number of cells secreting $IFN\gamma^+$ was then analysed by ELISPOT. The statistically significant increases are indicated (*$p<0.05$; $p<0.01$; *$p<0.005$).

FIG. 5: immunisation of transgenic mice for the HLA-A2 molecule using different peptide combinations A. Percentage of $CD8^+$/$IFN\gamma^+$ T lymphocytes after ex vivo restimulation of splenocytes with each of the peptides, alone or in combination. B', B" and B"'. Cytotoxic response of CD8 T lymphocytes after immunisation of mice with the different peptide combinations (C1-C6).

Figure 6:
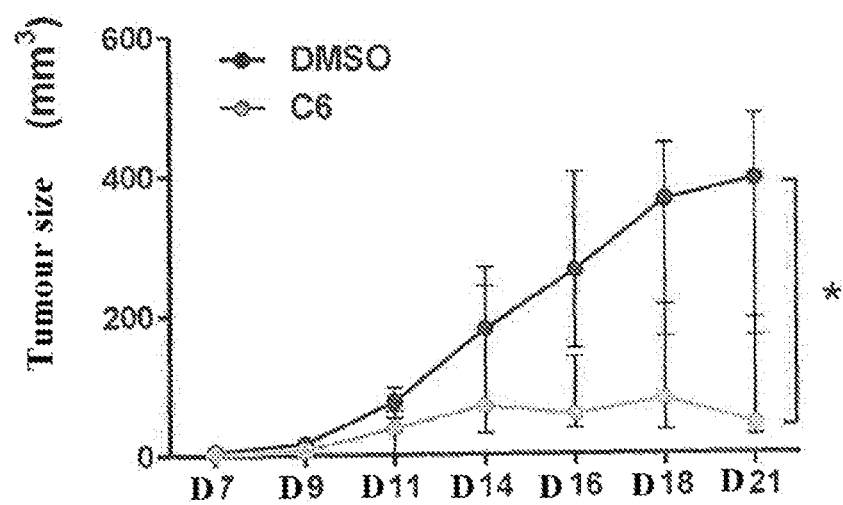

FIG. 6: antitumour effect of peptide combination C6 in the transgenic mouse model for HLA-A2 molecules. $1\times10^6$ D122-ppCT tumour cells were grafted under the skin in the flanks of the transgenic mice on day 0 (D0) The mice were then vaccinated under the skin at D0, D3, D4 and D14, with 100 μM of each peptide contained in the combination C6, and 25 μg of adjuvant. The size of the tumour is defined by the formula length*width*depth. The statistically significant difference in tumour growth is indicated (*$p<0.05$).

FIG. 7: potentiation of the antitumour response and of the control of tumour growth by combined immunotherapy. A. The combined therapy optimises control of the tumour growth. The NOD-scid Il2rγ$^{null}$ (NSG) mice have received a graft of Heu-nIR tumour fragments in the flank, then an adoptive transfer of human PBMC from healthy donors at day D10, followed at day D11 by an intravenous vaccination with the vaccine based on the peptide mixture C6, combined or not with an anti-PD1 monoclonal antibody from day D12. The tumour growth was recorded every two days until the end of the experiment. B. The mice treated with the combined therapy (vaccine+anti-PD-1) demonstrated the strongest reduction in the weight of the tumour, compared with mice treated by the vaccine alone (*$p<0.04$) or anti-PD-1 alone (*$p<0.03$). C. Cytokine production induced by the combined therapy in vivo. The levels of human IFN-γ plasmids in the serum of the treated or untreated mice were determined by ELISA before the end of the experiment (*$p<0.01$). D. Production of IFN-γ, granzyme B (GrmB) and perforin (Perf) by the splenocytes of treated and untreated mice The $CD8^+$ T cells producing IFN-γ, granzyme B (GrmB) and perforin (Perf) were evaluated by intracellular fluorescence analysis. The values correspond to the mean fluorescence intensity (MFI). *$p<0.05$; **$p<0.001$. The error bars represent the standard error of the mean (SEM).

FIG. 8: potentiation of the control of the tumour growth by combined immunotherapy. A. The combined therapy optimises control of the tumour growth. The NOD-scid Il2rγ$^{null}$ (NSG) mice have received a graft of Heu-nIR tumour fragments in the flank, then an adoptive transfer of human PBMC from healthy donors at day D10, followed at day D11 by an intravenous vaccination with the vaccine based on the peptide mixture C6a, combined or not with an anti-PD1 monoclonal antibody from day D12. The tumour growth was recorded every two days until the end of the experiment. B. The mice treated with the combined therapy (vaccine+anti-PD-1) showed the strongest reduction in the weight of the tumour, compared with mice treated by the anti-PD-1 alone.

EXAMPLE 1: IN VITRO STIMULATION OF PBMC OF PATIENTS BY 9- OR 10-AMINO-ACID PEPTIDES OF PREPROCALCITONIN

Materials and Methods
Peptides
The following peptides were selected:

```
ppCT9-17
                                        (SEQ ID NO: 4)
FLALSILVL;

ppCT16-25
                                        (SEQ ID NO: 5)
VLLQAGSLHA.

ppCT50-59
                                        (SEQ ID NO: 6)
LLAALVQDYV;

ppCT91-100
                                        (SEQ ID NO: 7)
CMLGTYTQDF;
```

Cells Used and Stimulation

The peripheral blood mononuclear cells (PBMC) of 11 patients with non-small cell lung cancer (NSCLC) were isolated from the peripheral blood by Ficoll. For each peptide, the PBMC were stimulated twice (D0 and D7) with 20 µM of peptide. The PBMC were cultivated for 2 weeks on 96-well plates, at a rate of 20 million cells/plate, on complete medium (RPMI 1640, 10% SAB, 1% sodium pyruvate, 0.1% penicillin/streptavidin) in the presence of IL-2 (20 IU/ml)+IL-4 (10 ng/ml)+IL-7 (10 ng/ml).

Analysis by Cytometry

After 15 days, the PBMC are again stimulated with 2.5 µM of the peptide used during the first stimulation step, in the presence of 100 µg/ml of Brefeldin A, and incubated for 6 hours at 37° C., 5% $CO_2$. The cells are then incubated for 20 minutes with an anti-CD8-APC antibody, then washed in PBS, fixed with PBS-formaldehyde 2% and permeabilised by BSA/saponin. They are then incubated with an anti-IFN-γ-PE antibody. The analysis is carried out by flow cytometry. The statistical study is performed using the Mann-Whitney test and the statistically significant increases are indicated (*$p<0.05$; $p<0.01$; *$p<0.005$).

Results

The results are illustrated in FIG. 2.

The analysis by flow cytometry of the response to the stimulation with the various 9- or 10-amino-acid peptides showed that the stimulation by the pCT9-17, ppCT16-25, ppCT50-59 and ppCT91-100 peptides leads to an increase of 1 to 4.5 times the base level of $CD8^+/INF\gamma^+$ T lymphocytes in the patients tested. The analysis of the different stimulation wells showed that this increase in the CD8 response is statistically significant (*$p<0.05$; $p<0.01$; *$p<0.005$). However, different patients do not respond in the same way to each of the peptides. Patients 1, 2, 6, 8 and 9 trigger a secretion of IFNγ by the CD8 T lymphocytes after stimulation by all the tested peptides, whereas patients 4, 5 and 7 only trigger a lymphocyte response after stimulation with peptides ppCT9-17 and ppCT50-59, while patient 3 triggers a response with peptides ppCT50-59 and ppCT91-100.

In conclusion, it appears that the peptides are immunogenic depending on the tested patient and allow an immune response via the CD8 T lymphocytes. Because of the variability of the response to the different peptides, a peptide combination would have a better chance of inducing an anti-ppCT response in the majority of patients included.

EXAMPLE 2: IN VITRO STIMULATION OF PATIENTS WITH SHORT 9-AA OR 10-AA PEPTIDES OR THE DIFFERENT PEPTIDE COMBINATIONS

Materials and Methods
Peptides
The following peptides were selected:

```
ppCT1-15:
                                        (SEQ ID NO: 1)
MGFQKFSPFLALSIL;

ppCT71-85:
                                        (SEQ ID NO: 2)
EREGSSLDSPRSKRC;

ppCT86-100:
                                        (SEQ ID NO: 3)
GNLSTCMLGTYTQDF;

ppCT9-17
                                        (SEQ ID NO: 4)
FLALSILVL;

ppCT16-25
                                        (SEQ ID NO: 5)
VLLQAGSLHA.

ppCT50-59
                                        (SEQ ID NO: 6)
LLAALVQDYV;

ppCT91-100
                                        (SEQ ID NO: 7)
CMLGTYTQDF;
```

Cells Used and Stimulation

The peripheral blood mononuclear cells (PBMC)) of 3 patients with non-small cell lung cancer were isolated from the peripheral blood by Ficoll, then stimulated twice (D0 and D7) with 20 µM of each of the peptides or with equimolar concentrations of 20 µM of each peptide described in FIG. 3. The PBMC are cultivated for 2 weeks on 96-well plates, at a rate of 20 million cells/plate, on complete medium (RPMI 1640, 10% SAB, 1% sodium pyruvate, 0.1% penicillin/streptavidin) in the presence of IL-2 (20 IU/ml)+IL-4 (10 ng/ml)+IL-7 (10 ng/ml).

Analysis by ELISPOT

After 15 days, the PBMC are recovered and incubated on ELISPOT plates at a rate of 100,000 cells per well, in the presence of medium with 2.5 µM of each peptide or with equimolar combinations of 2.5 µM of each peptide used for the stimulation. Plates are incubated for 15 to 18 hours at 37° C. and 5% $CO_2$. The IFNγ spots are revealed following the manufacturer's instructions (Gen-Probe Diaclone). The spots formed by the cells secreting IFNγ are counted and analysed using the C.T.L Immunospot system (Cellular Technology Ltd). The statistical study is performed using the Mann-Whitney test and the statistically significant increases are indicated (*$p<0.05$; $p<0.01$; *$p<0.005$).

Results

The results are illustrated in FIG. 4.

The analysis of the number of cells secreting IFNγ following the stimulation of PBMC of 3 patients using the combinations described in FIG. 3, demonstrated that the different combinations enable stimulation and hence amplification of the specific lymphocytes of these peptides. Indeed, a significant increase in the number of cells secreting IFNγ is observed for 3 combinations in patient 11, for 4 combinations in patient 10 and for the 6 combinations in patient 3.

Moreover, the stimulations by the combinations C2, C5 and C6 also increase the number of cells secreting IFNγ with respect to the stimulations by the peptides alone. These responses are patient dependent. Indeed, the stimulation of the PBMC of patient 3 by combinations C2, C5 and C6 increases the number of cells secreting IFNγ by a factor of 6 for C2, a factor of 3 for C5 and a factor of 2 for C6, whereas for patient 10, only the stimulation of PBMC with the combination C2 increases the number of cells secreting IFNγ by a factor of 3 and the stimulation of PBMC of patient 11 by the combinations C5 and C6 increases the number of cells secreting IFNγ by a factor of 3 for C5 and a factor of 2 for C6.

This result shows that the combination of a plurality of peptides derived from the ppCT antigen increases the immune response developed by CD8 T lymphocytes. Moreover, these results also demonstrate the advantage of using a peptide combination compared to single peptide in order to trigger an immune response in the majority of patients.

EXAMPLE 3: IMMUNISATION OF TRANSGENIC MICE WITH THE DIFFERENT PEPTIDE COMBINATIONS

Materials and Methods
Peptides

The following peptides were selected:

```
ppCT1-15:
                                        (SEQ ID NO: 1)
MGFQKFSPFLALSIL;

ppCT71-85:
                                        (SEQ ID NO: 2)
EREGSSLDSPRSKRC;

ppCT86-100:
                                        (SEQ ID NO: 3)
GNLSTCMLGTYTQDF;

ppCT9-17
                                        (SEQ ID NO: 4)
FLALSILVL;

ppCT16-25
                                        (SEQ ID NO: 5)
VLLQAGSLHA.

ppCT50-59
                                        (SEQ ID NO: 6)
LLAALVQDYV;

ppCT91-100
                                        (SEQ ID NO: 7)
CMLGTYTQDF;
```

Cells Used

The human TT tumour cell line (from a medullary thyroid tumour) and IGR-Heu tumour cell line (isolated from the NSCLC tumour of patient Heu), expressing the antigen ppCT, are used as target cells. The K562 cell line (from a patient having a chronic myeloid leukaemia) is used as the negative control. The Heu-EBV line (from B lymphocytes of patient Heu) is used to determine the specificity of the lysis. After marking with $^{51}$Cr, the Heu-EBV cells are incubated with the equimolar mixture having 20 μM of each peptide (described in FIG. 4).

Immunisation of Mice

The transgenic mice for the HLA-A2 molecules were immunised 4 times (D0, D7, D14 and D21), under the skin on the flank, with 100 μl of peptide combinations containing an equimolar mixture of 100 μM of each of the peptides and an adjuvant (25 μg of Poly (I:C)) (FIG. 4). At 28 days after the first injection, the mice were sacrificed and the splenocytes were recovered and cultivated overnight in complete medium (RPMI 1640, 10% FBS, 1% sodium pyruvate, 0.1% penicillin/streptavidin) in the presence of IL-2 (20 IU/ml).

Analysis by Cytometry and Analysis by Cytotoxicity Test

The next day, the splenocytes were stimulated with 2.5 μM of each of the peptides, alone or in combination, in the presence of 10 μg/ml of Brefeldin A and incubated for 6 hours at 37° C., 5% $CO_2$. The cells are then incubated for 20 minutes with an anti-CD8-PE antibody, then washed in PBS, fixed with PBS-formaldehyde 2% and permeabilised with BSA/saponin. They are then incubated with an anti-IFNγ-APC antibody. The analysis is carried out by flow cytometry.

For the analysis of the cytotoxic activity, the CD8 T lymphocytes were isolated from the splenocytes by negative depletion (Miltenyi Biotech). The cytotoxic activity of the CD8 T lymphocytes thus obtained, was evaluated by a chromium-51 ($^{51}$Cr) leaching test. The target cells (described in the paragraph above) are incubated for 1 hour at 37° C. in the presence of 20 μM of $^{51}$Cr. The cells are then washed with RPMI before being co-cultivated at 37° C. with the CD8 T lymphocytes at effector/target ratios of 50:1, 25:1 and 12:1. After 4 hours incubation, the concentration of leached $^{51}$Cr in the co-culture supernatant is measured. The percentage of lysis is calculated using the following formula:

$$\% \ lysis = \frac{(\text{leached chromium} - \text{leached chromium minimum})}{(\text{leached chromium maximum} - \text{leached chromium minimum})} \times 100$$

Results

Figure 5A:
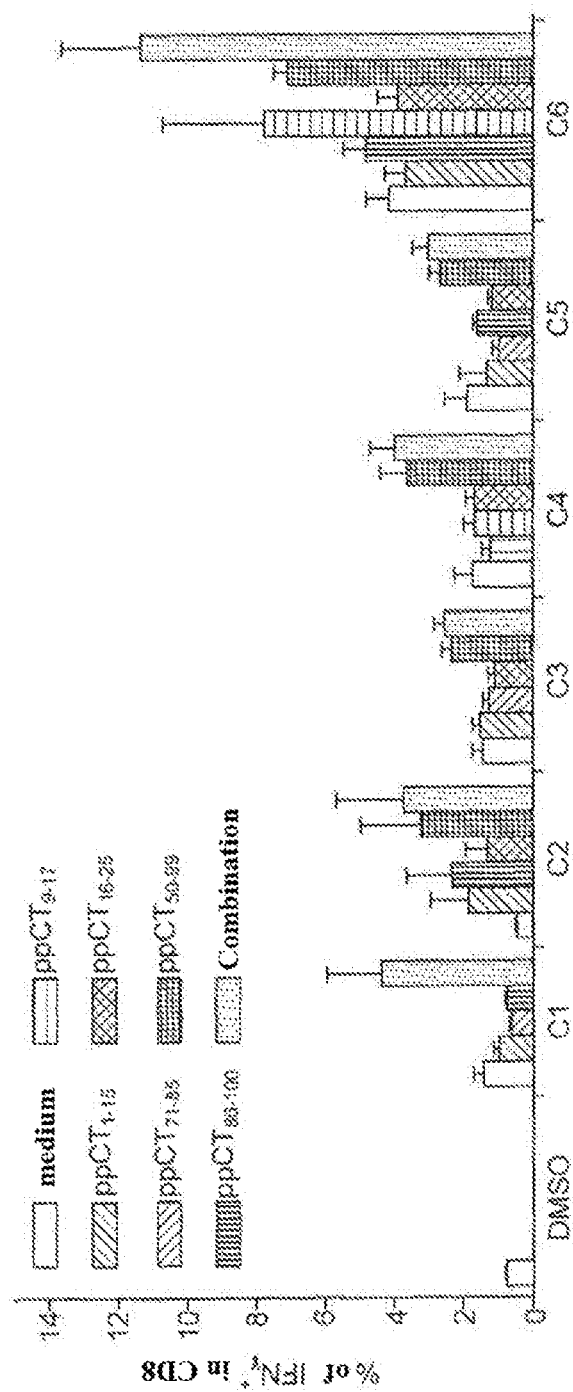

The flow cytometry analysis of the splenocytes isolated following immunisation of the mice with peptide combinations C1 to C6 shows an increase in the percentage of CD8 T lymphocytes expressing IFNγ (FIG. 5A). This increase is dependent on the combination used, involving a change by a factor of 3 to 13 (4.8 for C1, 3 for C2, 3.4 for C3, 5.5 for C4, 4.3 for C5 and 13.6 for C6). These results demonstrate that the immunisation of transgenic mice with the different peptide combinations enables the development of immune responses through the induction of CD8 T lymphocytes.

Moreover, the ex vivo stimulation with each of the peptides from the combination, demonstrates the additional effect of the combinations. For combination C1, it is seen that the response after ex vivo stimulation increases by a factor of 4.2, 5.2 and 4.6 with respect to ex vivo stimulations by the peptides ppCT1-15, ppCT71-85 and ppCT86-100 respectively. The same observation can be made on the effectiveness of the immune response via the CD8 T lymphocytes for all the combinations. Nevertheless, none of the combinations demonstrates the effect on the peptide ppCT50-59, due in particular to the strong response that it induces naturally.

Figure 5B:
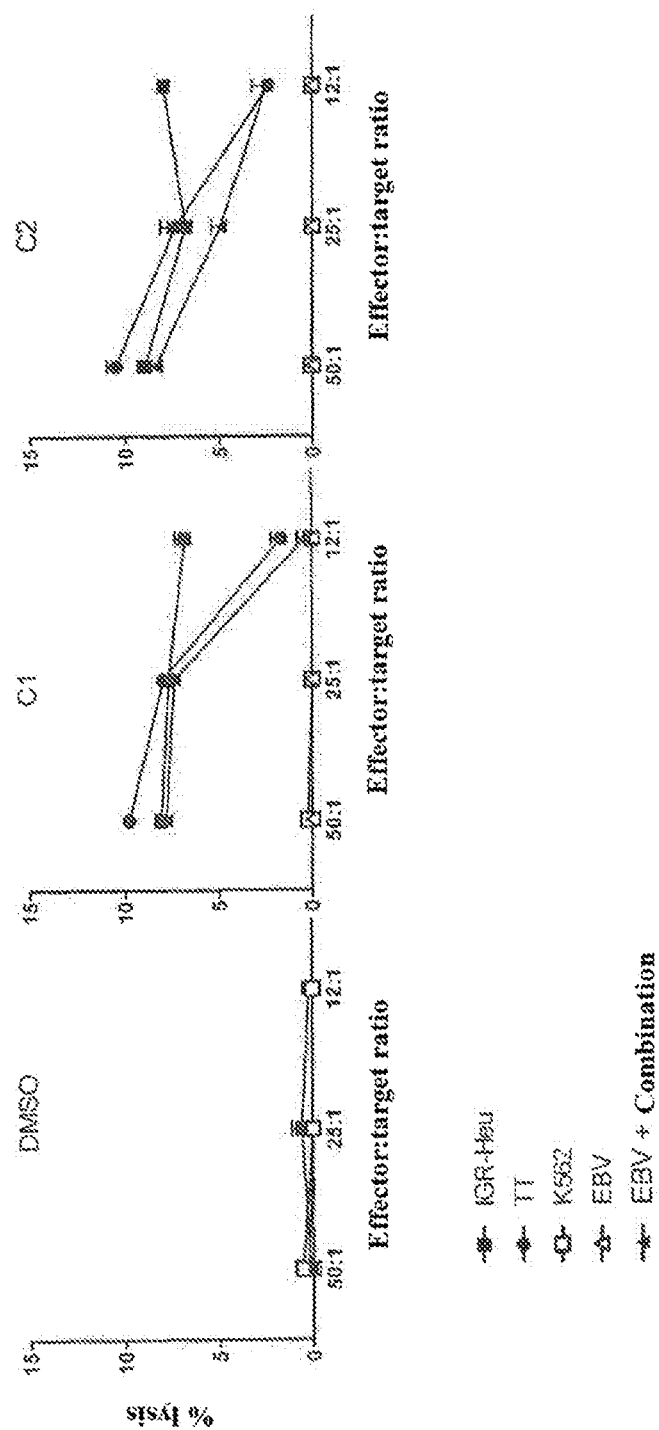
Figure 5B:
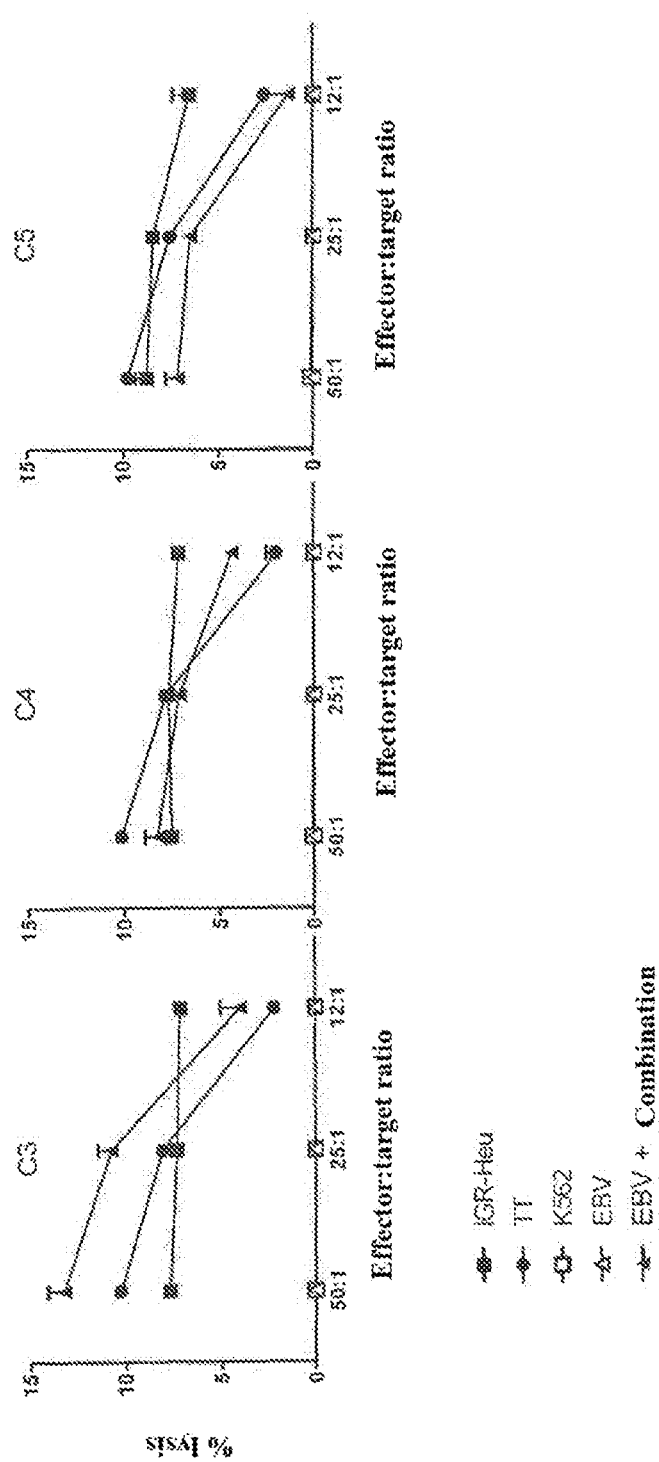
Figure 5B:
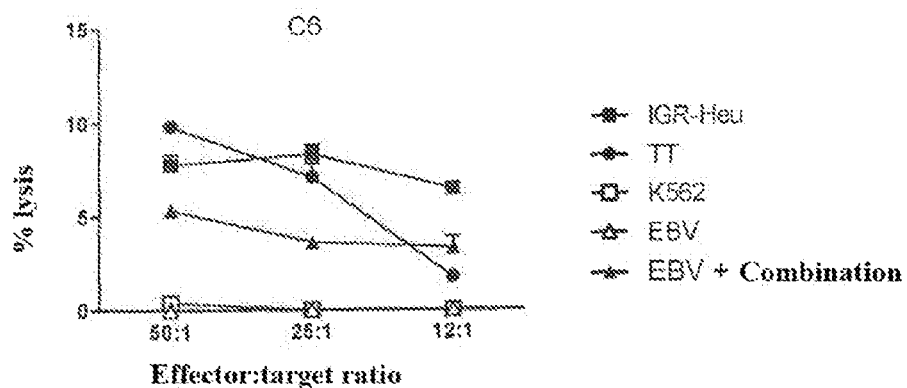

Finally, the CD8 T lymphocytes generated by the immunisations of the mice with the peptide combinations are capable of recognising and lysing, in a specific manner, the cells expressing antigen ppCT, such as IGR-Heu and TT (FIG. 5B). Indeed, FIG. 5B shows that the CD8 T lymphocytes from the splenocytes of non-immunised mice are not capable of lysing either the IGR-Heu tumour line or the TT tumour line, unlike the CD8 T lymphocytes from the splenocytes of immunised mice. Depending on the immunisation conditions, the lymphocytes lyse between 7 and 15% of cells expressing the antigen ppCT. The T lymphocytes do not lyse K562 cells or Heu-EBV cells, except when these are loaded with the peptide combination. This result demonstrates the specificity of the lysis obtained for the tumour cells expressing the antigen ppCT.

All of the results, obtained by the immunisation of transgenic mice, demonstrate that the use of peptide combinations can activate and increase the immune response exerted by CD8 T lymphocytes against cells expressing the antigen ppCT.

EXAMPLE 4: VACCINATION OF TRANSGENIC MICE WITH COMBINATION C6

Materials and Methods
Peptides
The following peptides were selected:

ppCT1-15:
MGFQKFSPFLALSIL;  (SEQ ID NO: 1)

ppCT86-100:
GNLSTCMLGTYTQDF;  (SEQ ID NO: 3)

ppCT9-17
FLALSILVL;  (SEQ ID NO: 4)

ppCT16-25
VLLQAGSLHA;  (SEQ ID NO: 5)

ppCT50-59
LLAALVQDYV.  (SEQ ID NO: 6)

Cells Used

The transgenic murine line LL2 (Lewis lung carcinoma) for molecules HLA-A2 (line D122) was infected with a lentivirus expressing GFP and which codes for the human antigen ppCT. Then, $10^6$ cells were injected under the skin on the flank of the mice.

Immunisation of Mice

The transgenic mice for the HLA-A2 molecules were vaccinated 4 times (D0, D4, D7 and D14), under the skin on the flank, with 100 µl of peptide combination C6 containing an equimolar mixture of 100 µM of each of the peptides and an adjuvant (25 µg of Poly (I:C)).

Monitoring Tumour Growth

After the graft of tumour cells, the weight of the mice was monitored every day, and the tumours were measured every 2-3 days starting from the 7th day. The size is calculated in $mm^3$ in the following way: length×width×depth. The statistically significant tumour growth difference is calculated by a t-test and indicated (*p<0.05).

Results

In the transgenic mice model for HLA-A2 molecules, having a tumour expressing ppCT, vaccination with combination C6 induces a reduction in tumour growth that is significant with respect to the non-vaccinated mice. Indeed, at the end of 21 days, one in three mice vaccinated had a tumour of size 190 $mm^3$ whereas the three control mice had developed a tumour with a mean size of 350 $mm^3$ (FIG. 6).

This result demonstrates the capacity of vaccination with combination C6 to generate an immune response that is effective against tumours expressing ppCT, demonstrating the advantage of using these combinations in antitumour immunotherapy.

EXAMPLE 5: VACCINATION OF HUMANISED MICE WITH COMBINATION C6 ALONE OR COMBINED WITH AN ANTI-PD-1

Materials and Methods

Mice, Human Tumour Graft and Transfer of Human PBMC.

The NOD-scid Il2rγ$^{null}$ mice (NSG; Jackson Laboratory), aged 3-4 weeks, were grafted under the skin with the human tumour Heu-nIR, generated by implantation of the human tumour cell line IGR-Heu, transfected beforehand with chemokine CCL5 (RANTES) and adhesion molecule ICAM-1 in order to optimise the infiltration of the tumour by T lymphocytes and their capacity to interact with the target cells, maintained in the nude mice (Franciszkiewicz et al., Cancer Res., 2009, 69, 6249-6255). Then 10 days later, when the tumours are palpable, $2.10^7$ peripheral blood mononuclear cells (PBMC) from healthy allogenic human donors, tested in vitro beforehand for their capacity to induce responses in CD8 T cells directed against antigenic peptides ppCT, were injected intravenously into the tails of the mice. The recombinant IL-15 (3 µg/mouse/day) was then administered intraperitoneally to promote the survival of the T cells.

Peptides

The peptides used are:
combination C6 consisting of peptides ppCT9-17, ppCT16-25 and ppCT50-59, which comprise epitopes restricted to HLA-A and long peptides ppCT1-15 and ppCT86-100, and
combination C6a also comprising peptides of combination C6, three peptides restricted to HLA-B7: ppCT7-15 (SEQ ID NO: 19), ppCT46-54 (SEQ ID NO: 20) and ppCT79-88 (SEQ ID NO: 21).

Immunisation of Mice and Monitoring of Tumour Growth

The NSG mice, having received an Heu-nIR tumour graft and an adoptive transfer of PBMC, were vaccinated 2 times at an interval of one week, with 100 µl of peptide combination C6 or C6a containing an equimolar mixture of each of the peptides and adjuvant (25 µg of poly (I:C), one day after the transfer of PBMC. For the combined therapy, the vaccinated mice were treated intravenously with an anti-hPD-1 antibody (220 mg/injection) or a control antibody of the same isotype (220 mg of non-relevant hIgG4), every two days from the second day after transfer of PBMC.

The weight of the mice was monitored every day and the tumours were measured every 2 days for only 3 or 4 weeks in order to avoid graft-versus-host disease (GVHD). Plasma samples were taken on the last day of the experiment, before sacrifice of the mice, and stored at −80° C. until use. The mice were sacrificed and the tumours weighed and then dissociated for analysis of the infiltrating T lymphocytes (TIL) by flow cytometry. In parallel, the spleen was sampled and the capacity of the splenocytes to secrete gamma interferon (IFN-γ) after ex vivo stimulation with the peptide combination was tested.

ELISA Tests

The level of human IFN-γ in the plasma of the vaccinated and non-vaccinated mice was measured using a commercially available ELISA kit (Human IFN-γ ELISA Set; BD OptEIA™, BD Biosciences), according to the manufacturer's recommendations. All the samples were measured in duplicate.

Antibodies and Immunofluorescence Analyses

The antibodies used are human monoclonal antibodies anti-CD45, CD3, CD8, CD4, CD44, PD-1, perforin, granzyme B and IFN-γ, as well as isotypical mouse and rabbit controls (Miltenyi) and human monoclonal antibodies anti-CD69, CD62L, CD49a, CD45RO and CCR7 (Invitrogen). The blocking experiments were carried out with human monoclonal antibody anti-PD-1 and non-relevant control antibody of the same either type. These phenotypic analyses were carried out by direct immunofluorescence, using a BD™ LSR II flow cytometer. The data were analysed using the FlowJo® software.

Statistical Analyses

The statistical analyses were performed using Prism 6.0 software (GraphPad software). The results from the different groups are compared using the t-test for the independent samples. A value of P<0.05 for a bilateral test is considered to be statistically significant.

Results

The antitumour effect of the peptide vaccine based on the antigenic peptides of preprocalcitonin was evaluated in a humanised mouse model NOD-scid (NSG). To invert the depletion of activated T lymphocytes and to advantageously potentiate the beneficial therapeutic effect of the vaccine against cancer, this active immunotherapy strategy has been combined with a clinically-used anti-PD1 monoclonal antibody. The NSG mice received an Heu-nIR tumour graft and then an adoptive transfer of PBMC from healthy HLA-A2+ donors, and were then immunised with a vaccine based on combination C6 or C6a, alone or in combination with a PD-1 immune checkpoint inhibitor.

Figure 7A:
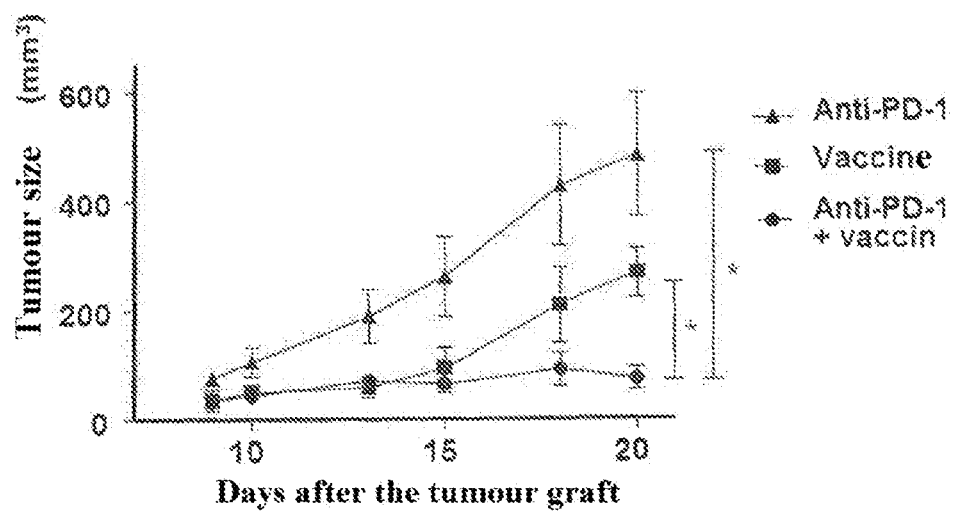
Figure 7B:
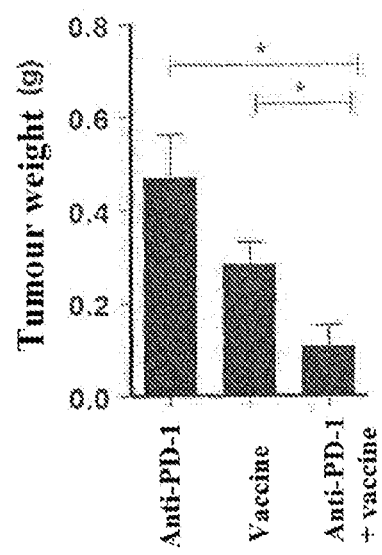

The results show that the treatment of humanised mice with the combined immunotherapy induces a much stronger reaction against tumour growth than each of the monotherapies (FIG. 7A). The tumour growth control is correlated with a reduction in the weight of tumours in mice treated with the combined therapy, compared to those mice treated with the vaccine or the anti-PD1 alone (FIG. 7B).

Figure 7C:
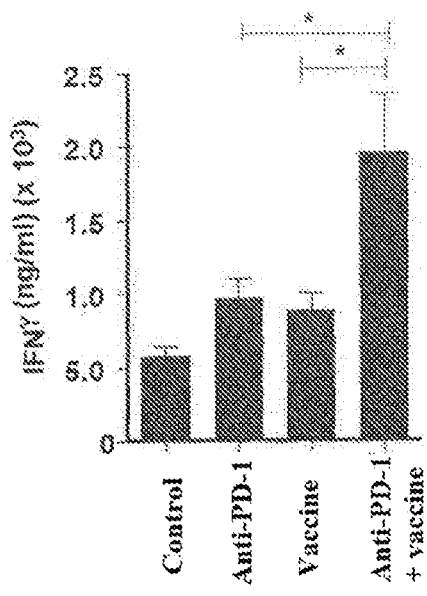

The production of human IFN-γ by the three groups of mice was then evaluated to analyse whether the reduction in tumour growth was associated with an increase in the immune response. An increase by a factor of 2 in the level of human IFN-γ in the plasma was detected in the serum of the mice treated with the combined immunotherapy, when compared to the mice treated with each of the therapies alone (FIG. 7C). In addition, intracellular staining of splenocytes of mice treated with the combined therapy indicates that the $CD8^+$ T cells express higher levels of IFN-γ, granzyme B and perforin (FIG. 7D). These results indicate that, compared to the two monotherapies, the combined therapy is more effective for controlling the growth of tumours, and that this effect is correlated with more effective functions of the T cells.

Figure 8A:
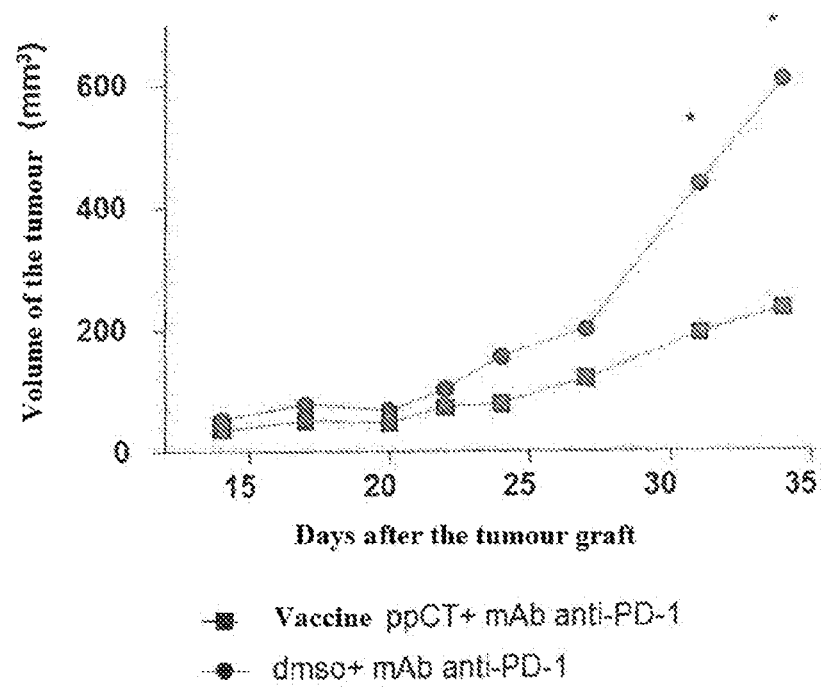
Figure 8B:
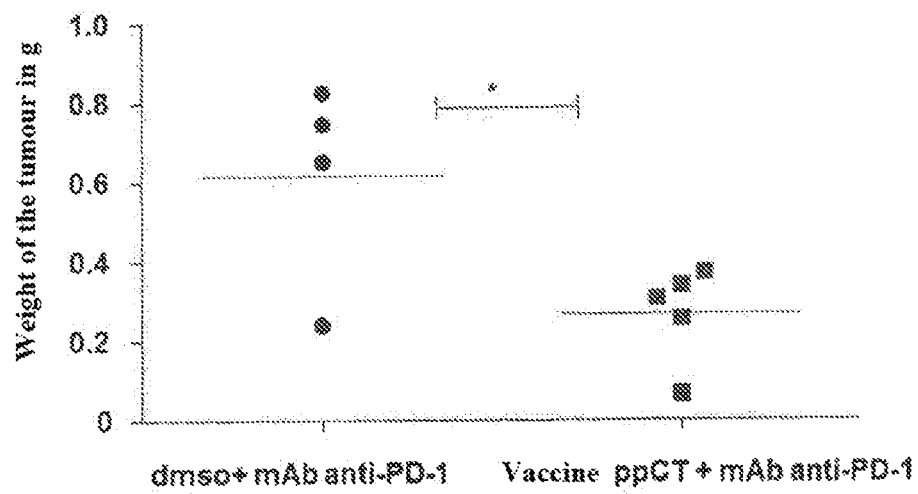

The antitumour effect of the combined therapy is observed with the two peptide combinations tested; combination C6, which comprises peptides restricted to HLA-A2 and long peptides (FIGS. 7A and 7B), and combination C6a, which in addition to the peptides of combination C6 also comprises peptides restricted to HLA-B7 (FIGS. 8A and 8B).

The combined approach induces an increase in the secretion of IFN-γ by CD8 T cells and the infiltration of the tumour by the activated T cells, correlated with a reduction in tumour growth. Consequently, the combined therapy represents an interesting strategy for treating tumours which have escaped CD8 T cell immunity or conventional immunotherapies.

The invention claimed is:

1. A method of antitumor immunotherapy, comprising administering to a human subject an immunogenic composition comprising two peptides chosen from the sequences consisting of SEQ ID NO: 3 and 6, and a pharmaceutically acceptable adjuvant in an amount effective to induce an antitumor immune response in the human subject.

2. The method according to claim 1, which is for immunotherapy of tumors expressing calcitonin, or of pathologies associated with a high serum level of calcitonin, precalcitonin, or prepro-α-CGRP.

3. The method according to claim 1, which is for immunotherapy of medullary thyroid carcinoma or pulmonary carcinoma.

4. The method according to claim 1, which is for immunotherapy of a tumor having cells which do not express TAP peptide transporters.

5. The method according to claim 1, wherein said human subject is HLA-A*0201 positive.

6. The method according to claim 1, wherein the immunogenic composition further comprises at least two peptides chosen from the sequences consisting of SEQ ID NOs: 1 to 7.

7. The method according to claim 1, wherein the immunogenic composition further comprises at least two additional peptides chosen from the sequences consisting of SEQ ID NOs: 1 and 5.

8. The method according to claim 7, wherein the immunogenic composition comprises at least one additional peptide chosen from the sequences consisting of SEQ ID NO: 2 or 4.

9. The method according to claim 1, wherein the immunogenic composition comprises a combination of peptides chosen from the combination of sequences consisting of SEQ ID NOs: 1, 2, 3, 5 and 6, the combination of sequences consisting of SEQ ID NOs: 1, 3, 4, 5 and 6, the combination of sequences consisting of SEQ ID NOs: 1, 3, 5 and 6, and the combination of sequences consisting of SEQ ID NOs: 3, 4, 5 and 6.

10. The method according to claim 1, wherein the immunogenic composition comprises antigen-presenting cells loaded with said peptide sequences.

11. The method according to claim 1, further comprising administering at least one immune checkpoint inhibitor.

12. The method according to claim 1, further comprising administering at least one additional peptide chosen from the sequences consisting of SEQ ID NO: 19, 20 or 21.

13. The method according to claim 1, wherein the immunogenic composition is an antitumor vaccine.

* * * * *

SEQUENCE LISTING

```
<160> NUMBER OF SEQ ID NOS: 21

<210> SEQ ID NO 1
<211> LENGTH: 15
<212> TYPE: PRT
<213> ORGANISM: Artificial Sequence
<220> FEATURE:
<223> OTHER INFORMATION: synthetic peptide ppCT1-15

<400> SEQUENCE: 1

Met Gly Phe Gln Lys Phe Ser Pro Phe Leu Ala Leu Ser Ile Leu
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: synthetic peptide ppCT71-85

<400> SEQUENCE: 2

Glu Arg Glu Gly Ser Ser Leu Asp Ser Pro Arg Ser Lys Arg Cys
1               5                   10                  15
```

```
<210> SEQ ID NO 3
<211> LENGTH: 15
<212> TYPE: PRT
<213> ORGANISM: Artificial Sequence
<220> FEATURE:
<223> OTHER INFORMATION: synthetic peptide ppCT86-100

<400> SEQUENCE: 3

Gly Asn Leu Ser Thr Cys Met Leu Gly Thr Tyr Thr Gln Asp Phe
1               5                   10                  15

<210> SEQ ID NO 4
<211> LENGTH: 9
<212> TYPE: PRT
<213> ORGANISM: Artificial Sequence
<220> FEATURE:
<223> OTHER INFORMATION: synthetic peptide ppCT9-17

<400> SEQUENCE: 4

Phe Leu Ala Leu Ser Ile Leu Val Leu
1               5

<210> SEQ ID NO 5
<211> LENGTH: 10
<212> TYPE: PRT
<213> ORGANISM: Artificial Sequence
<220> FEATURE:
<223> OTHER INFORMATION: synthetic peptide ppCT16-25

<400> SEQUENCE: 5

Val Leu Leu Gln Ala Gly Ser Leu His Ala
1               5                   10

<210> SEQ ID NO 6
<211> LENGTH: 10
<212> TYPE: PRT
<213> ORGANISM: Artificial Sequence
<220> FEATURE:
<223> OTHER INFORMATION: synthetic peptide ppCT50-59

<400> SEQUENCE: 6

Leu Leu Ala Ala Leu Val Gln Asp Tyr Val
1               5                   10

<210> SEQ ID NO 7
<211> LENGTH: 10
<212> TYPE: PRT
<213> ORGANISM: Artificial Sequence
<220> FEATURE:
<223> OTHER INFORMATION: synthetic peptide ppCT91-100

<400> SEQUENCE: 7

Cys Met Leu Gly Thr Tyr Thr Gln Asp Phe
1               5                   10

<210> SEQ ID NO 8
<211> LENGTH: 15
<212> TYPE: PRT
<213> ORGANISM: Artificial Sequence
<220> FEATURE:
<223> OTHER INFORMATION: synthetic peptide ppCT45-60

<400> SEQUENCE: 8

Glu Ala Arg Leu Leu Leu Ala Ala Leu Val Gln Asp Tyr Val Gln
1               5                   10                  15

<210> SEQ ID NO 9
```

```
<210> SEQ ID NO 9
<211> LENGTH: 10
<212> TYPE: PRT
<213> ORGANISM: Artificial Sequence
<220> FEATURE:
<223> OTHER INFORMATION: synthetic peptide ppCT1-10

<400> SEQUENCE: 9

Met Gly Phe Gln Lys Phe Ser Pro Phe Leu
1               5                   10

<210> SEQ ID NO 10
<211> LENGTH: 9
<212> TYPE: PRT
<213> ORGANISM: Artificial Sequence
<220> FEATURE:
<223> OTHER INFORMATION: synthetic peptide ppCT3-12

<400> SEQUENCE: 10

Phe Gln Lys Phe Pro Phe Leu Ala Leu
1               5

<210> SEQ ID NO 11
<211> LENGTH: 10
<212> TYPE: PRT
<213> ORGANISM: Artificial Sequence
<220> FEATURE:
<223> OTHER INFORMATION: synthetic peptide ppCT5-14

<400> SEQUENCE: 11

Lys Phe Ser Pro Phe Leu Ala Leu Ser Ile
1               5                   10

<210> SEQ ID NO 12
<211> LENGTH: 10
<212> TYPE: PRT
<213> ORGANISM: Artificial Sequence
<220> FEATURE:
<223> OTHER INFORMATION: synthetic peptide ppCT6-15

<400> SEQUENCE: 12

Phe Ser Pro Phe Leu Ala Leu Ser Ile Leu
1               5                   10

<210> SEQ ID NO 13
<211> LENGTH: 10
<212> TYPE: PRT
<213> ORGANISM: Artificial Sequence
<220> FEATURE:
<223> OTHER INFORMATION: synthetic peptide ppCT87-96

<400> SEQUENCE: 13

Asn Leu Ser Thr Cys Met Leu Gly Thr Tyr
1               5                   10

<210> SEQ ID NO 14
<211> LENGTH: 10
<212> TYPE: PRT
<213> ORGANISM: Artificial Sequence
<220> FEATURE:
<223> OTHER INFORMATION: synthetic peptide ppCT88-97

<400> SEQUENCE: 14

Leu Ser Thr Cys Met Leu Gly Thr Tyr Thr
1               5                   10

<210> SEQ ID NO 15
<211> LENGTH: 10
```

```
<212> TYPE: PRT
<213> ORGANISM: Artificial Sequence
<220> FEATURE:
<223> OTHER INFORMATION: synthetic peptide ppCT96-105

<400> SEQUENCE: 15

Tyr Thr Gln Asp Phe Asn Lys Phe His Thr
1               5                   10

<210> SEQ ID NO 16
<211> LENGTH: 10
<212> TYPE: PRT
<213> ORGANISM: Artificial Sequence
<220> FEATURE:
<223> OTHER INFORMATION: synthetic peptide ppCT41-50

<400> SEQUENCE: 16

Thr Leu Ser Glu Asp Glu Ala Arg Leu Leu
1               5                   10

<210> SEQ ID NO 17
<211> LENGTH: 10
<212> TYPE: PRT
<213> ORGANISM: Artificial Sequence
<220> FEATURE:
<223> OTHER INFORMATION: synthetic peptide ppCT53-62

<400> SEQUENCE: 17

Ala Leu Val Gln Asp Tyr Val Gln Met Lys
1               5                   10

<210> SEQ ID NO 18
<211> LENGTH: 9
<212> TYPE: PRT
<213> ORGANISM: Artificial Sequence
<220> FEATURE:
<223> OTHER INFORMATION: synthetic peptide ppCT58-66

<400> SEQUENCE: 18

Tyr Val Gln Met Lys Ala Ser Glu Leu
1               5

<210> SEQ ID NO 19
<211> LENGTH: 9
<212> TYPE: PRT
<213> ORGANISM: artificial sequence
<220> FEATURE:
<223> OTHER INFORMATION: synthetic peptide ppCT7-15

<400> SEQUENCE: 19

Ser Pro Phe Leu Ala Leu Ser Ile Leu
1               5

<210> SEQ ID NO 20
<211> LENGTH: 9
<212> TYPE: PRT
<213> ORGANISM: artificial sequence
<220> FEATURE:
<223> OTHER INFORMATION: synthetic peptide ppCT46-54

<400> SEQUENCE: 20

Glu Ala Arg Leu Leu Leu Ala Ala Leu
1               5

<210> SEQ ID NO 21
<211> LENGTH: 10
<212> TYPE: PRT
```

```
<213> ORGANISM: artificial sequence
<220> FEATURE:
<223> OTHER INFORMATION: synthetic peptide ppCT79-88

<400> SEQUENCE: 21

Ser Pro Arg Ser Lys Arg Cys Gly Asn Leu
1               5                   10
```